United States Patent
Saini et al.

(10) Patent No.: US 9,961,905 B2
(45) Date of Patent: May 8, 2018

(54) METHODS AND COMPOSITIONS FOR REDUCING CONTAMINATION ON FOOD CONTACT SURFACES

(71) Applicant: WTI, Inc., Jefferson, GA (US)

(72) Inventors: Jasdeep K. Saini, Athens, GA (US); Kevon Ledgerwood, Jefferson, GA (US); Wolfgang Ludwig, Jefferson, GA (US)

(73) Assignee: WTI, INC., Jefferson, GA (US)

( * ) Notice: Subject to any disclaimer, the term of this patent is extended or adjusted under 35 U.S.C. 154(b) by 0 days. days.

(21) Appl. No.: 15/097,104

(22) Filed: Apr. 12, 2016

(65) Prior Publication Data

US 2017/0290342 A1    Oct. 12, 2017

(51) Int. Cl.
| | | |
|---|---|---|
| *A61K 36/752* | (2006.01) | |
| *A01N 65/36* | (2009.01) | |
| *A01N 37/02* | (2006.01) | |
| *A61L 2/18* | (2006.01) | |

(52) U.S. Cl.
CPC ............. *A01N 65/36* (2013.01); *A01N 37/02* (2013.01); *A61L 2/18* (2013.01); *A61L 2202/20* (2013.01)

(58) Field of Classification Search
CPC .................................................. A61K 36/752
USPC ....................................................... 424/736
See application file for complete search history.

(56) References Cited

U.S. PATENT DOCUMENTS

| | | | | |
|---|---|---|---|---|
| 6,436,342 | B1 * | 8/2002 | Petri | A01N 59/00 422/28 |
| 7,306,815 | B2 * | 12/2007 | Gourdin | A61K 31/352 424/725 |
| 2001/0046979 | A1 | 11/2001 | Roselle et al. | |
| 2003/0158540 | A1 * | 8/2003 | Washington | A61F 5/441 604/544 |
| 2007/0105741 | A1 * | 5/2007 | Bowker | A01N 59/00 510/375 |
| 2008/0075804 | A1 | 3/2008 | Alam et al. | |
| 2009/0004122 | A1 * | 1/2009 | Modak | A61K 8/345 424/49 |
| 2009/0175806 | A1 * | 7/2009 | Modak | A61K 8/365 424/58 |
| 2010/0172848 | A1 * | 7/2010 | Modak | A01N 65/00 424/58 |
| 2011/0311600 | A1 * | 12/2011 | Polzin | A01N 33/12 424/409 |
| 2012/0201902 | A1 * | 8/2012 | Modak | A01N 31/02 424/618 |
| 2013/0065959 | A1 | 3/2013 | Ho et al. | |
| 2013/0287918 | A1 | 10/2013 | Fischer et al. | |
| 2013/0295230 | A1 | 11/2013 | Maniga et al. | |
| 2014/0242198 | A1 * | 8/2014 | Modak | A01N 31/08 424/736 |
| 2014/0255525 | A1 * | 9/2014 | Smith | A61K 47/46 424/727 |

OTHER PUBLICATIONS

Healey, J. Website document entitled "This Stuff Will Make You Want to Clean Your Home's Surfaces!" Feb. 4, 2013. 11 pages. Obtained from http://www.scratchmommy.com.*
Gremont. L. Website document entitled 7 Homemade Vinegar Cleaning Recipes. Jan. 29, 2014. 5 pages. Obtained from http://www.homemademommy.net.*
McFall, S. Website document entitled "Homemade Citrus Infused Vinegar for Cleaning". Nov. 12, 2012. 10 pages. Obtained from http://mymerrymessylife.com.*
Penniston et al. J. Endourol. 2008. vol. 22, No. 3, pp. 567-570.*
International Search Report and Written Opinion for PCT International Application No. PCT/US2017/026968, Jul. 17, 2017, 13.

* cited by examiner

*Primary Examiner* — Chris R Tate
(74) *Attorney, Agent, or Firm* — F. Brent Nix, Esq.; Johnson, Marcou & Isaacs, LLC

(57) ABSTRACT

Embodiments disclosed herein provide methods for decontaminating food contact surfaces using a fine spray/mist that comprise an antimicrobial composition comprising an organic acid and an organic citrus extract. The spray application reduces the microbiological populations on the surface of food contact surfaces, including potential pathogens, thereby reducing cross-contamination and improving food safety. The composition described herein can be use to target a number of microbiological pathogens, including *L. monocytogenes*, which is a known cross-contaminant in retail environments such as deli counters and slicers due to its ability to grow at refrigerated temperatures and moist environments making it a known cause of post-processing contamination of ready-to-eat food products.

25 Claims, 8 Drawing Sheets

FIG. 5

METHODS AND COMPOSITIONS FOR REDUCING CONTAMINATION ON FOOD CONTACT SURFACES

TECHNICAL FIELD

The invention relates to method for reducing microbiological contamination on food contact surfaces, such as deli-slicers and meat counters, using a fine spray/mist method of applying compositions comprising organic acids in combination with organic citrus extracts.

BACKGROUND

*Listeria monocytogenes* is a pathogenic bacterium that causes listeriosis and has been implicated in several outbreaks linked to consumption of ready-to-eat (RTE) sliced deli meats. RTE meat slicers especially in retail delis provide ideal conditions for certain bacteria, like *Listeria*, to colonize and grow. Sliced RTE meats can become contaminated with this pathogen during the slicing process and may pose a serious public health concern. Hence, effective interventions are needed to control this pathogen and prevent cross-contaminations from deli slicers on to the RTE food product being sliced. Accordingly, methods for controlling such contamination that are effective and safe for use with equipment used to prepare food products is needed.

SUMMARY

The embodiments disclosed herein are directed to antimicrobial compositions comprising an organic acid and an organic citrus extract and use of said compositions in methods for reducing microbial contamination on food contact surfaces. The organic acid may be acetic acid, formic acid, propionic acid, butyric acid, valeric acid, caproic acid, oxalic acid, lactic acid, malic acid, citric acid, benzoic acid, carbonic acid, or a combination thereof. In one example embodiment, the organic acid is acetic acid. The organic citrus extract is derived from a blend of two or more citrus fruit extracts. In certain example embodiments, the organic citrus extract is a blend of two or more citrus fruit extracts, excluding grapefruit derived extracts. Food contact surfaces that may be treated with the antimicrobial composition include, but are not limited to, stainless steel surfaces, glass surfaces, rubber or wood surfaces. The antimicrobial compositions may be used to reduce microbiological contamination caused by a number of bacteria and fungal species, including *Listeria* species. In certain example embodiments, the antimicrobial compositions are applied to the food contact surfaces as a fine mist or spray.

In another aspect, the embodiments disclosed herein are directed to methods for reducing microbiological contamination on food contact surfaces comprising applying the antimicrobial compositions described herein in an effective amount to reduce or eliminate one or more microbial populations on a food contact surface. The antimicrobial composition may be applied as a fine spray or mist. The food contact surface may be a wood surface, a plastic surface, a rubber surface, a glass surface, or a stainless steel surface. Microbial populations that may be reduced or eliminated from food contact surfaces using the methods disclosed herein include bacterial and fungal species.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 5 is a graph showing *L. monocytogenes* populations recovered on modified oxford medium from stainless steel coupons (n=5) at various time points after treatment with an example antimicrobial composition disclosed herein.

DETAILED DESCRIPTION OF THE EXAMPLE EMBODIMENTS

Overview

Figure 1:
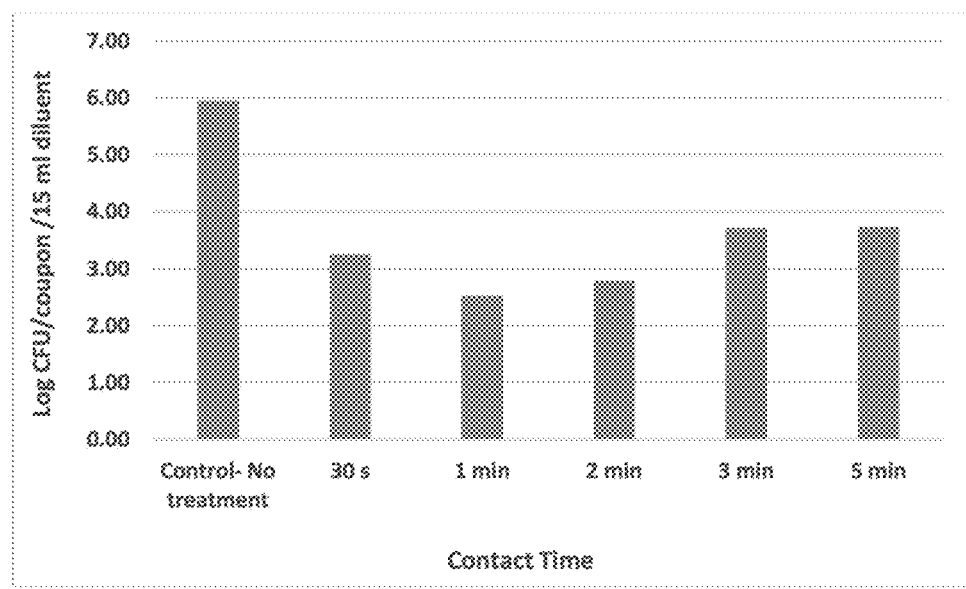
FIG. 1 is a graph showing *Listeria monocytogenes* populations recovered on modified oxford medium from stainless steel coupons post treatment with an example antimicrobial composition disclosed herein (4.4 mL spray nozzle).

Embodiments disclosed herein provide methods for decontaminating food contact surfaces using a fine spray/mist that comprise an antimicrobial composition comprising an organic acid and an organic citrus extract. The spray application reduces the microbiological populations on the surface of food contact surfaces, including potential pathogens, thereby reducing cross-contamination and improving food safety. The composition described herein can be used to target a number of microbiological pathogens, including *L. monocytogenes*, which is a known cross-contaminant in retail environments such as deli counters and slicers due to its ability to grow at refrigerated temperatures and moist environments making it a known cause of post-processing contamination of ready-to-eat food products. The composition is applied to a surface to be treated for a period of time sufficient to reduce or eliminate the microbial contamination.

In certain example embodiments, the antimicrobial composition comprises an organic acid and an organic citrus extract. The antimicrobial composition may also further comprise a masker and an emulsifier. The antimicrobial composition may be used to reduce or eliminate microbiological contamination on food contact surfaces. Example food contact surfaces include, but are not limited to, wood surfaces, glass surfaces, plastic surface, rubber surfaces and stainless steel surfaces. In certain example embodiments, the antimicrobial compositions achieve at least a 10%, at least a 15%, at least a 20%, at least a 25%, at least a 30%, at least 35%, at least 40%, at least 45%, at least 50%, at least 55%, at least 60%, at least 65%, at least 70%, at least 75%, at least 80%, at least 85%, at least 90%, at least 95%, at least 97%, at least 98%, or at least 99% reduction in microbial populations on the food contact surface treated.

The composition may be applied as a fine spay or mist on the surface to be treated. In certain example embodiments, the spray or mist is applied at a rate of 1 mL/10 seconds of spray, 2 mL/10 seconds of spray, 3 mL/10 seconds of spray, 4 mL/10 seconds of spray, 5 mL/10 seconds of spray, 6 mL/10 seconds of spray, 7 mL/10 seconds of spray, 8 mL/10 seconds of spray, 9 mL/10 seconds of spray, 10 mL/10 seconds of spray, 11 mL/10 seconds of spray, 12 mL/10 seconds of spray, 13 mL/10 seconds of spray, 14 mL/10 seconds of spray, 15 mL/10 seconds of spray, 16 mL/10 seconds of spray, 17 mL/10 seconds of spray, 18 mL/10 seconds of spray, 19 mL/10 seconds of spray, 20 mL/10 seconds of spray, 21 mL/10 seconds of spray, or 22 mL/10 seconds of spray. The spray may be applied using a 4.4 mL, 8 mL, or 22 mL nozzle. The amount of spray applied is based on the surface area to be treated. In certain example embodiments, an amount of spray applied is sufficient to form a thin film on the surface to be treated. The amount of time a spray should be dispensed in order to apply a thin film to a surface to be treated can be determined based on the type of spray nozzle used.

In certain example embodiments, the antimicrobial composition is allowed to remain in contact with the treated surface for at least 3 hours, at least 2 hours, at least 60 mins, at least 55 mins, at least 50 mins, at least 45 mins, at least 40 mins, at least 35 mins, at least 30 mins, at leas 25 mins, at least 20 mins, at least 15 mins, at least 10 mins, at least 5 min, at least 3 min, at least 2 min, at least 1 min, at least 30 second, at least 20 second, at least 10 seconds, at least 5 seconds, or at least 1 second before food is brought in contact with the treated surface.

The organic acid may include acetic acid, formic acid, propionic acid, butyric acid, valeric acid, caprioc acid, oxalic acid, lactic acid, malic acid, citric acid, benzoic acid, carbonic acid, or a combination thereof. In certain example embodiments, the organic acid is acetic acid and/or a consumable salt equivalent thereof. In certain example embodiments, the acetic acid is sourced from a vinegar. Source vinegar materials may include, for example, corn, sugar cane, glacial acetic, and apple cider. Source vinegar materials may include, for example, corn, sugar cane, glacial acetic, and apple cider. The vinegar may be prepared using standard buffering agents known in the art. In certain example embodiments, the vinegar comprises 0.5% to 8% acetic acid. In certain other example embodiments, the vinegar comprises 1% to 4% acetic acid. In certain example embodiments, the source vinegar is a buffered vinegar with an acidity of approximately 1.2% and pH of 6.9.

The organic acid may be at a concentration of 5% to 99.5%, 10% to 99.5%, 15% to 99.5%, 20% to 99.5%, 25% to 99.5%, 30% to 99.5%, 35% to 99.5%, 40% to 99.5%, 45% to 99.5%, 50% to 99.5%, 55% to 99.5%, 60% to 99.5%, 65% to 99.5%, 70% to 99.5%, 75% to 99.5%, 80% to 99.5%, 85% to 99.5%, 90% to 99.5%, 91% to 99.5%, 92% to 99.5%, 93% to 99.5%, 94% to 99.5%, 95% to 99.5%, 96% to 99.5%, 97% to 99.5%, or 98% to 99.5%, 5% to 50%, 10% to 50%, 15% to 50%, 20% to 50%, 25% to 50%, 30% to 50%, 35% to 50%, 40% to 50%, 45% to 50%, 50% to 75%, 55% to 75%, 60% to 75%, 65% to 75%, or 70% to 75% (w/v). In one example embodiment, the organic acid is at a concentration between 95% and 99.5% (w/v).

In certain example embodiments, the organic acid has a pH of approximately 5.5 to approximately 7.3, approximately 5.6 to approximately 7.3, approximately 5.7 to approximately 7.3, approximately 5.8 to approximately 7.3, approximately 5.9 to approximately 7.3, approximately 6.0 to approximately 7.3, approximately 6.1 to approximately 7.3, approximately 6.2 to approximately 7.3, approximately 6.3 to approximately 7.3, approximately 6.4 to approximately 7.3, approximately 6.5 to approximately 7.3, approximately 6.6 to approximately 7.3, approximately 6.7 to approximately 7.3, approximately 6.8 to approximately 7.3, approximately 6.9 to approximately 7.3, approximately 7.0 to approximately 7.3, approximately 7.1 to approximately 7.3, approximately 7.2 to approximately 7.3, approximately 5.5 to approximately 7.1, approximately 5.5 to approximately 5.9, approximately 5.5 to approximately 5.8, approximately 5.5 to approximately 5.7, approximately 5.5 to approximately 5.6. As used in the context of describing pH value ranges above, "approximately" means a pH value within 0.05 of the stated pH values.

The organic citrus extract is derived from citrus fruits, including but not limited to amanatsu, balady citron, bergamot orange, bitter orange, blood orange, Buddha's hand, calamondin, cam sanh, citron, clementine, Corsican citron, desert lime, etrog, finger lime, Florentine citron, grapefruit, Greek citron, hyuganatsu, iyokan, kabosu, kaffir lime, key lime, kinnow, kiyomi, kumquat, lemon, lime, mandarin orange, mangshanyegan, Meyer lemon, Moroccan citron, myrtle-leaved orange, orange, oroblanco, Persian lime, pomelo, ponderosa lemon, rangpur, round lime, satsuma, shangjuan, shonan gold, sudachi, sweet limetta, Taiwan tangerine, tangelo, tangerine, tangor, ugli fruit, yuzu, or combination thereof. In certain example embodiments, the citrus extract is prepared from the albedo and flavedo layers of the citrus fruits. In certain example embodiments, the citrus extract is prepared from *Citrus aurantium* amara fruit extract, *Citrus reticulate* fruit extract, and *Citrus aurantium* sinesis peel extract. The extract may be suspended in glycerin from a natural source or other suitable carrier. In certain example embodiments, the glycerin is a vegetable glycerin. In certain example embodiments, the organic citrus extract is a blend of two or more of the citrus fruits listed above. In certain example embodiments, the organic citrus extract is a blend of two or more citrus fruits, but not including grapefruit derived extracts. In certain example embodiments, the composition may have a honey color. In certain example embodiments, the composition may be at least 70%, at least 75%, at least 80%, at least 85%, at least 90%, at least 95%, at least 96%, at least 97%, at least 98%, at least 99%, or 100% soluble in water. In certain example embodiments, the composition may be a crystalline liquid. In certain example embodiments, the organic citrus fruit extract comprises citrus bioflavonoids and citrus polyphenols at ≥4% concentration and are an active ingredients in the formulation. In certain example embodiments, the organic citrus extract is derived from certified organic citrus fruits. In certain example embodiments, the carrier is from a certified organic plant material.

In certain example embodiments, the organic citrus extract is at a concentration of 0.1% to 5%, 0.1% to 4.5%, 0.1% to 4.0%, 0.1% to 3.5%, 0.1% to 3.0%, 0.1% to 2.5%, 0.1% to 2.0%, 0.1% to 1.5%, 0.1% to 1.0%, 0.1% to 0.9%, 0.1% to 0.8%, 0.1% to 0.7%, 0.1% to 0.6%, 0.1% to 0.6%, 0.1% to 0.5%, 0.1% to 0.4%, 0.1% to 0.3%, 0.11% to 0.2%, 0.2% to 1%, 0.3% to 1%, 0.4% to 1%, 0.5% to 1%, 0.6% to 1%, 0.7% to 1%, 0.8% to 1%, 0.9% to 1%, 1% to 5%, 1.5% to 5%, 2% to 5%, 2.5% to 5%, 3% to 5%, 3.5% to 4%, or 4.5% to 5% (w/v).

In certain example embodiments, the organic citrus extract has a pH of approximately 2 to approximately 3.5, approximately 2 to approximately 3.4, approximately 2 to approximately 3.3, approximately 2 to approximately 3.2, approximately 2 to approximately 3.1, approximately 2 to approximately 3, approximately 2 to approximately 2.9, approximately 2 to approximately 2.8, approximately 2 to approximately 2.7, approximately 2 to approximately 2.6, approximately 2 to approximately 2.5, approximately 2 to approximately 2.4, approximately 2 to approximately 2.3, approximately 2 to approximately 2.2, approximately 2 to approximately 2.1, approximately 2.1 to approximately 3.5, approximately 2.2 to approximately 3.5, approximately 2.3 to approximately 3.5, approximately 2.4 to approximately 3.5, approximately 2.5 to approximately 3.5, approximately 2.6 to approximately 3.5, approximately 2.7 to approximately 3.5, approximately 2.8 to approximately 3.5, approximately 2.9 to approximately 3.5, approximately 3 to approximately 3.5, approximately 3.1 to approximately 3.5, approximately 3.2 to approximately 3.5, approximately 3.3 to approximately 3.5, or approximately 3.4 to approximately 3.5.

The antimicrobial composition may optionally further comprise a masker. Any commercially available masker suitable for suppressing bitterness and acidity may be used. In one example embodiment the masker is a naturally derived masker. In certain example embodiments, the masker may be at a concentration of approximately 0.05% to 0.2%, 0.05% to 0.1%, 0.05% to 0.09%, 0.05% to 0.08%, 0.05% to 0.07%, or 0.05% to 0.06% w/v.

The antimicrobial composition may optionally also comprise an emulsifier, used as a processing aid. Any commercially available emulsifier suitable for allowing stable liquid suspension may be used. In certain example embodiments, the emulsifier may be at a concentration of approximately 0.1% to 0.15%, 0.1% to 0.2%, 0.5% to 1%, 1% to 1.5, 1.5% to 1.9% or at levels ≤2% w/v.

The antimicrobial compositions described herein may be used to reduce microbial contamination on food contact surfaces from one or more microbes. The microbe may be a pathogenic microbe. In certain example embodiments, the microbe is a bacteria. The bacteria may be a psychrotroph, a coliform, a lactic acid bacteria, or a spore-forming bacteria. In certain example embodiments, the bacteria is a *Staphylococcus* species, a *Pseudomonas* species, a *Micrococcus* species, an *Aerococcus* species, a *Lactococcus* species, a *Leuconostoc* species, a *Streptococcus* species, a *Bacillus* species, a *Clostridium* species, a *Eubacteria* species, an *Enterococcus* species, a *Listeria* species, or a combination thereof. In certain example embodiments, the bacteria is a *Listeria* species. In certain example embodiments, the *Listeria* species is *L. monocytogenes*.

In certain example embodiments the microbe a yeast. In certain example embodiments, the fungi is a yeast. Example yeast may include, but are not limited to, a *Geotrichum* species, a *Saccharomyces* species, a *Hansenula* species, a *Candida* species, a *Kluyveromyces* species, a *Debaryomyces* species, a *Pichia* species, or combination thereof.

The invention is further described in the following examples, which do not limit the scope of the invention described in the claims.

EXAMPLES

Example 1

Bacterial Cultures and Inoculum Preparation:

Bacterial Cultures were obtained from American Type Culture Collection (ATCC). A five-strain (ATCC 19112, 19118, 19115, 13932, and 19111) cocktail of *Listeria monocytogenes* was used for inoculation of coupon. For inoculum preparation, freeze-dried cultures were grown in Tryptic Soy Broth (TSB) and fresh overnight 24 hr grown cultures were used. Each strain was combined in to a single mixed culture suspension to obtain a five-strain cocktail. The cell density of the inoculum was determined by spread plating and incubating the plates at 35° C. for 24 hr. The target inoculum level for this study was 6-7 log CFU/coupon.

Sample Preparation:

Polished stainless steel coupons were cleaned and autoclaved for use. Binder clips were attached to the coupons to allow hanging them from a small rod.

Inoculation of Samples:

Sterile stainless steel coupons were dipped in a 24 hr grown *L. monocytogenes* five-strain cocktail for 30 seconds and then hung to dry in a biosafety cabinet to allow bacterial attachment for 30-40 min. Excess inoculum on the inoculum was allowed to drip down.

Treatment of Samples:

Samples were treated with the antimicrobial solution using the spray/mist method using aerosolized cans under a biosafety cabinet. The antimicrobial was applied in different ways to assess its effect on the bacterium attached to the stainless steel coupon surface.

Treatment Formulation:

Vinegar

Organic Citrus extract

Masker

Emulsifier

Spray Cans Used:

4.4 ml nozzle (dispenses 4.4 ml of antimicrobial when sprayed for 10 s)

8 ml nozzle (dispenses 8 ml of antimicrobial when sprayed for 10 s)

Bacterial Enumeration:

After treatment application, each stainless steel coupon was individually placed in a 50 ml sterile conical tube with 15 ml of 0.1% sterile peptone diluent. Bacterial cells attached on the surface of coupon were dislodged by vortexing for 1 min. Serial dilutions were then prepared and spread plated on to selective media for *Listeria monocytogenes*, modified Oxford Medium (MOX). The plates were incubated at 35° C. for 48 h.

Test 1: 4.4 ml Nozzle and Individually Treated Coupons

Figure 2:
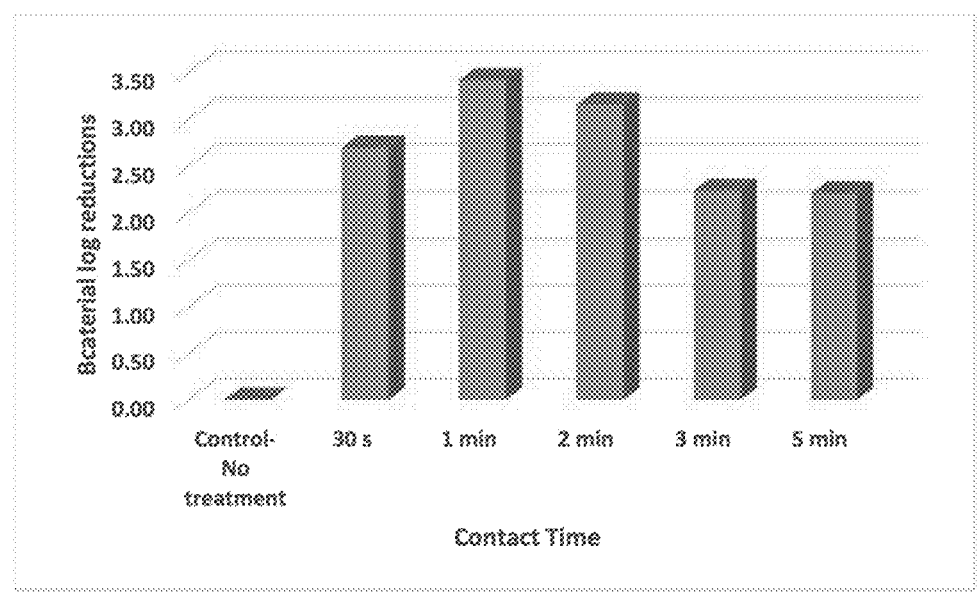
FIG. 2 is a graph showing reduction in *L. monocytogenes* populations on stainless steel coupons due to treatment with an example antimicrobial composition disclosed herein.

Sterile stainless steel coupons were surface inoculated with bacterial cocktail. 4.4 ml spray nozzle was used for antimicrobial composition application. Each coupon was individually sprayed with the antimicrobial composition for 10 secs on both sides, amounting to a 4.4 ml total antimicrobial composition on the surface of each coupon. The coupons were then held for 30 sec, 1 min, 2 min, 3 min and 5 min to allow for exposure to the antimicrobial composition. After the specified contact time, bacterial enumeration on the surface post treatment was performed. Control samples received no treatment and indicated initial levels of bacterial populations attached to the surface of the stainless steel coupons. Total number of samples analyzed were as follows: Control (n=16), 30 s (n=9), 1 min (n=9), 2 min (n=9), 3 min (n=14), 5 min (n=9). The data was generated from 3 separate days of testing and samples were added together to obtain an average for each subset. The results presented are based on an average of each treatment subset. Highest bacterial reductions were seen with 1 min antimicrobial contact time. See FIGS. 1 and 2.

Test 2: 8 ml Nozzle and Individually Treated Coupons

Figure 3:
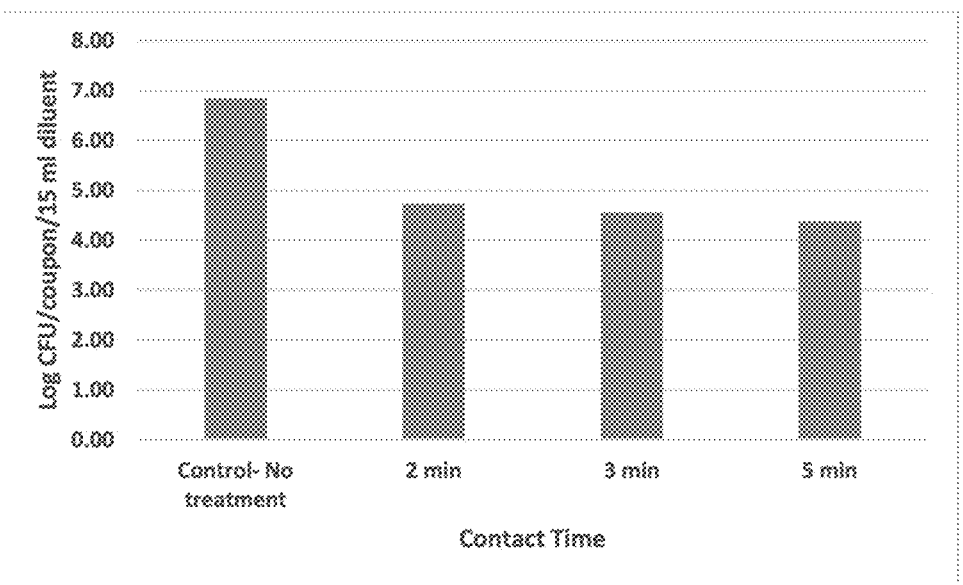
FIG. 3 is a graph showing reduction in *L. monocytogenes* populations recovered on modified oxford medium from stainless steel coupons post-treatment with an example antimicrobial composition disclosed herein (8 mL spray nozzle).
Figure 4:
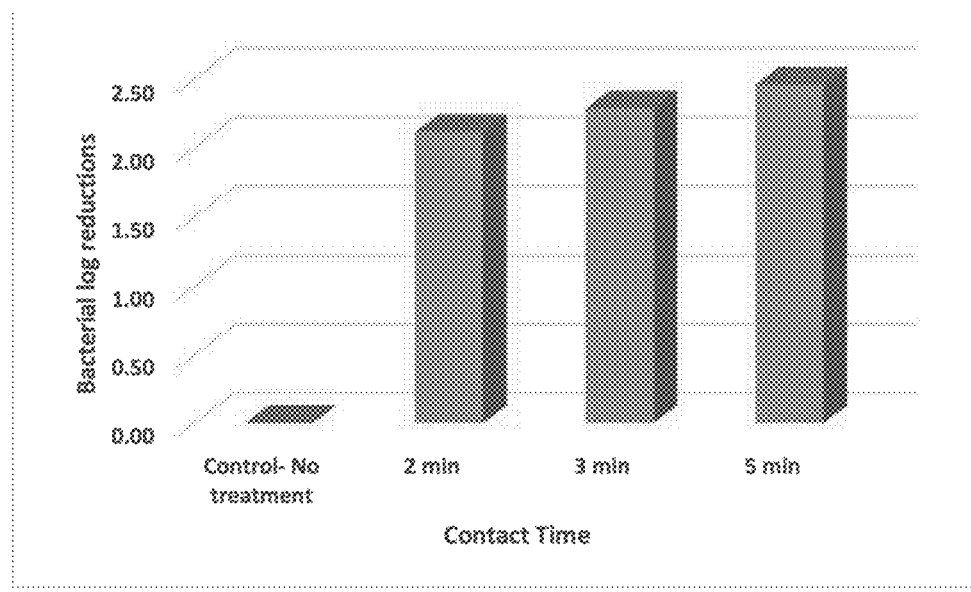
FIG. 4 is a graph showing reduction in *L. monocytogenes* populations on stainless steel coupons due to treatment with an example antimicrobial composition disclosed herein (8 mL spray nozzle).

Sterile stainless steel coupons were surface inoculated with bacterial cocktail. 8 ml spray nozzle was used for antimicrobial application. Each coupon was individually sprayed with the antimicrobial for 10 sec on both sides, amounting to 8 ml total antimicrobial composition on the surface of each coupon. The coupons were then held for 2 min, 3 min and 5 min to allow exposure to antimicrobial. After specified contact time, bacterial enumeration on the surface post treatment was performed. Control samples received no treatment and indicated initial levels of bacterial populations attached to the surface of the stainless steel coupons. Total number of samples analyzed were as follows: Control (n=3), 2 min (n=4), 3 min (n=4), 5 min (n=4). The results presented are based on average of each treatment subset. Bacterial reductions increased with increased contact time with the antimicrobial composition. See FIGS. 3 and 4.

Test 3: 8 ml Nozzle and Bulk Sprayed Coupons

Testing was continued to determine the effect of a non-specific dosage application of the antimicrobial treatment on the stainless steel coupon surface. This was performed to mimic food processing surface area conditions where the area to which the treatment applied may vary and precise application based on surface area may not be possible. Thirty sterile stainless steel coupons were surface inoculated with bacterial cocktail. 8 ml spray nozzle was used for antimicrobial composition application. The coupons were then divided in to 6 subsets and treated as below:

T1—Control (n=5, no treatment) Samples received no treatment and indicated initial levels of bacterial populations attached to the surface of the stainless steel coupons.

T2—Bulkspray 8 ml for 10 s. All coupons were sprayed together using spray can with 8 ml spray nozzle T3—Reinoculation In order to mimic re-contamination scenario in a food processing area, e.g. delis, samples were re-inoculated with low level (approx. 4 log cfu/ml) of five-strain *L. monocytogenes* cocktail by dipping coupons for 15 s in the cocktail).

T4—Bulk spray 8 ml for 10 s. All coupons were sprayed together using spray can with 8 ml spray nozzle.

T5—Reinoculation was repeated as performed in T3

T6—Bulk spray 8 ml for 10 s Same as T2 and T4

Figure 5:
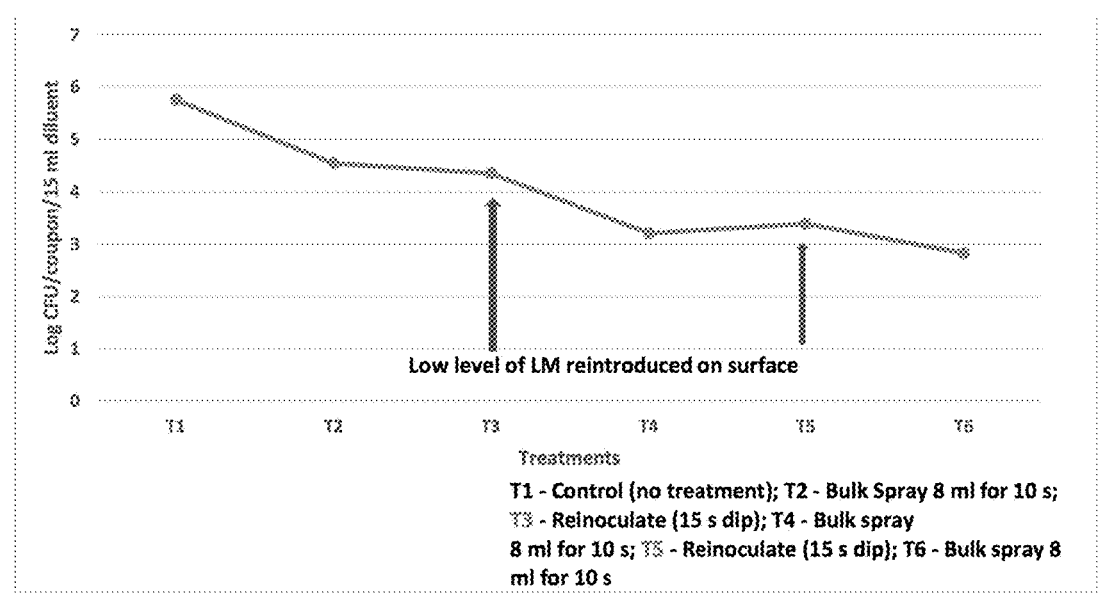
Figure 6:
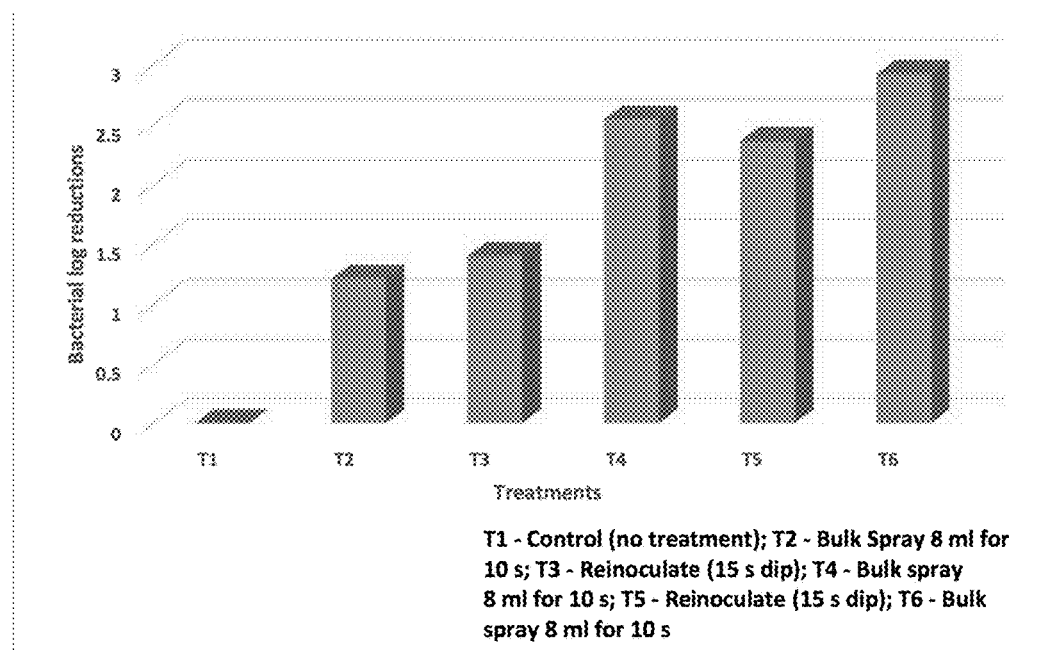
FIG. 6 is a graph showing reduction in *L. monocytogenes* population on stainless steel coupons (n=5) at various time points after treatment with an example antimicrobial composition disclosed herein.

The results presented are based on average (n=5) of each treatment subset. See FIGS. 5 and 6.

Test 4: 8 mL Nozzle and Bulk Sprayed Coupons

This was a modification of test 3 to evaluate if the initial bacterial load could be reduced even further by increasing the amount of antimicrobial composition applied at treatment 2 stage. In test 4, treatment 2, an 8 ml nozzle was used to spray all the coupons together for 20 sec.

Thirty sterile stainless steel coupons were surface inoculated with bacterial cocktail. 8 ml spray nozzle was used for antimicrobial application. The coupons were then divided in to 6 subsets and treated as below:

T1—Control (n=5, no treatment) Samples received no treatment and indicated initial levels of bacterial populations attached to the surface of the stainless steel coupons.

T2—Bulkspray 8 ml for 20 s. All coupons were sprayed together using spray can with 8 ml spray nozzle T3—Reinoculation In order to mimic re-contamination scenario in a food processing area, e.g. delis, samples were re-inoculated with low level (approx. 4 log cfu/ml) of five-strain *L. monocytogenes* cocktail by dipping coupons for 15 s in the cocktail)

T4—Bulk spray 8 ml for 10 sec. All coupons were sprayed together using spray can with 8 ml spray nozzle T5—Reinoculation-Reinoculation was repeated as performed in T3

T6—Bulk spray 8 ml for 10 s—same as T2 and T4

Figure 7:
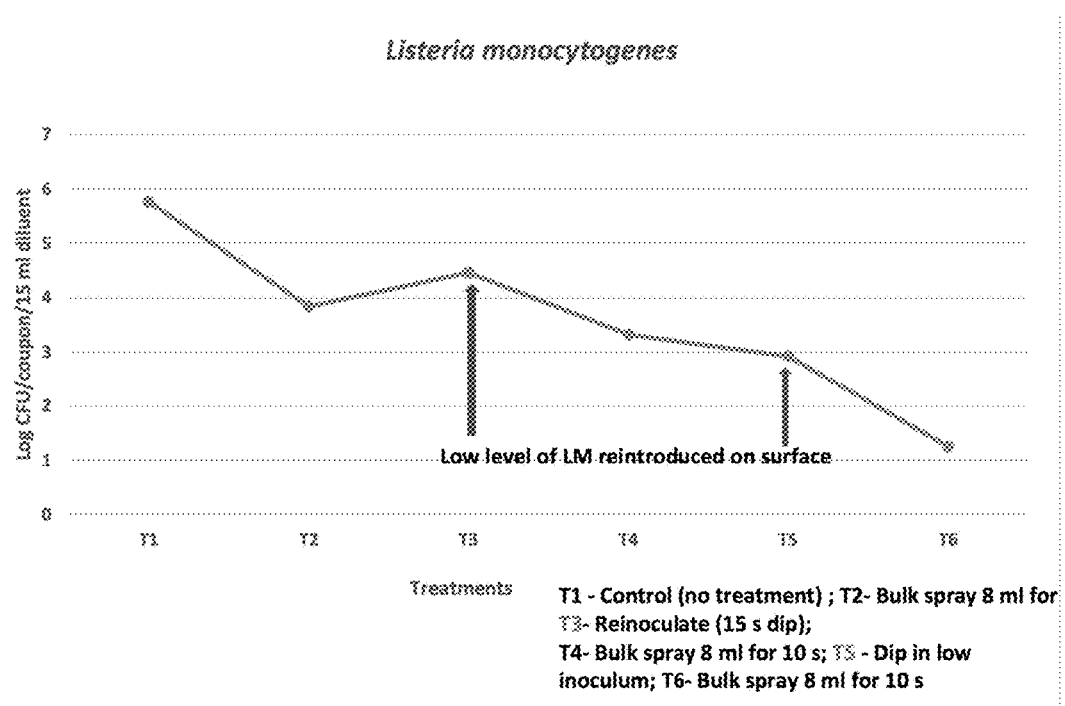
FIG. 7 is a graph showing *L. monocytogenes* population recovered on modified oxford medium from stainless steel coupons (n=5) at various time points after treatment with an example antimicrobial composition disclosed herein.
Figure 8:
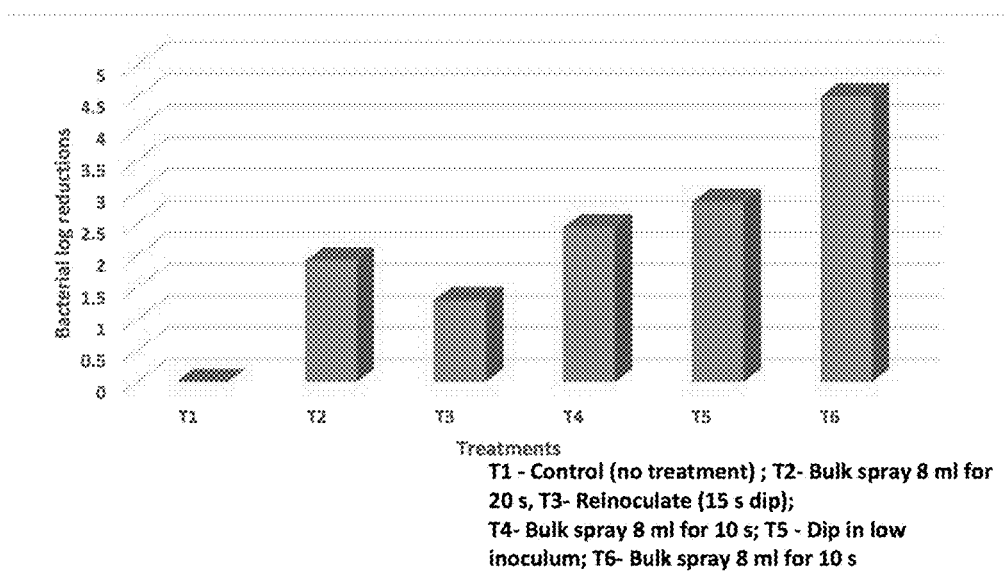
FIG. 8 is a graph showing reduction in *L. monocytogenes* population on stainless steel coupons (n=5) at various time points after treatment with an example antimicrobial composition disclosed herein.

The results presented are based on average (n=5) of each treatment subset. See FIGS. 7 and 8.

Test 5: 8 ml Nozzle and Bulk Sprayed Coupons

This was a modification of test 3 and 4 to evaluate effectiveness of antimicrobial spray on the surface by allowing antimicrobial to dry on the coupon surface before re-introduction of the pathogen on the surface and then allowing it to attach again for 30 min before re-applying treatment. This test would mimic food processing and handling conditions in a regular ongoing work shift where decontamination and re-contamination happens throughout the processing time period.

Thirty sterile stainless steel coupons were surface inoculated with bacterial cocktail. 8 ml spray nozzle was used for antimicrobial application. The coupons were then divided in to 6 subsets and treated as below:

T1—Control (n=5, no treatment)—Samples received no treatment and indicated initial levels of bacterial populations attached to the surface of the stainless steel coupons.

T2—Bulk spray 8 ml for 20 sec—All coupons were sprayed together using spray can with 8 ml spray nozzle and allowed to dry for 1 h with antimicrobial spray on the surface.

T3—In order to mimic re-contamination scenario in a food processing area, e.g., delis, samples were re-inoculated with low level (approx. 4 log cfu/ml) of five-strain *L. monocytogenes* cocktail by dipping coupons for 15 s in the cocktail). The coupons were allowed to dry for 30 min to allow re-attachment of bacterial cells.

T4—Bulk spray 8 ml for 10 s—All coupons were sprayed together using spray can with 8 ml spray nozzle and allowed to dry for 1 h with antimicrobial on the surface T5—Reinoculation was repeated as performed in T3

T6—Bulk spray 8 ml for 10 sec—Same as T2 and T4

The results presented are based on average (n=5) of each treatment subset. The results indicate that bacterial cells are unable to attach the surface in the presence of an example antimicrobial compositions disclosed herein. Bacterial log reductions continue to increase as more antimicrobial composition is applied on the surface in spite of re-contamination.

Example 2—Food Contact Surface Testing

Stainless Steel Surface

A five strain cocktail of *Listeria monocytogenes* was used to inoculate a representative food contact stainless steel surface (surface area 2419.5 cm$^2$) using the sponge method. Sterile sponge moistened with the five-strain cocktail suspension was used to inoculate the surface. The bacterial cultures were allowed to attach on the surface for 20 min. Spray treatment (8 ml/10 s) was used to treat the surface. Following treatment was used:

Treatment—20 s spray, 1 h hold time
Control—Non treatment

Sponge samples were then taken to enumerate bacterial population on the surface before and after treatments. Modified oxford medium (MOX) was used and plates were incubated at 35° C. for 24 hours. The results indicate reduction in bacterial populations due to treatment.

TABLE 1

| Sample | Bacterial Count Recovered | Bacterial Reduction |
|---|---|---|
| Control (No Treatment) | 21 CFU/cm$^2$ | |
| Treatment (1 hr hold time) | 0.62 CFU/cm$^2$ | 20.38 CFU/cm$^2$ |

Treatment of HDPE Cutting Board

A five strain cocktail of *Listeria monocytogenes* was used to inoculate two cutting boards, (surface areas 644.35 cm$^2$ and 769.35 cm$^2$) using the sponge method. Sterile sponge moistened with the five-strain cocktail suspension was used to inoculate the surface. The bacterial cultures were allowed to attach on the surface for 20 min. Spray treatment (8 ml/10 s) was used to treat these surfaces. Sponge samples were taken before and after treatment from the cutting boards. Bacteria were enumerated on modified oxford medium (MOX)

TABLE 2

| Cutting Board Area 769 cm$^2$ | Bacterial Count Recovered | Bacterial Reduction |
|---|---|---|
| Control (No Treatment) | 2.94 Log CFU/cm | |
| Treatment (1 hr hold time) | 1.72 Log CFU/cm | 1.22 Log CFU/cm$^2$ |

TABLE 3

| Cutting Board Area 769 cm$^2$ | Bacterial Count Recovered | Bacterial Reduction |
|---|---|---|
| Control (No Treatment) | 4.67 Log CFU/cm$^2$ | |
| Treatment (10 sec spray with 8 ml nozzle) | 2.69 Log CFU/cm$^2$ | 1.98 CFU/cm2 |

TABLE 4

| Cutting Board Area 644.35 cm$^2$ | Bacterial Count Recovered | Bacterial Reduction |
|---|---|---|
| Control (No Treatment) | 4.43 Log CFU/cm$^2$ | |
| Treatment (10 s spray with 8 ml nozzle, 3 min hold time) | 3.07 Log CFU/cm$^2$ | 1.36 Log CFU/cm2 |

Total Aerobic Count

Cutting boards (surface areas 644.35 cm$^2$ and 769.35 cm$^2$) were inoculated with total aerobic bacteria using sponge method. Bacterial cultures were allowed to attach for 20 min. Spray treatment (8 ml/10 s) was applied for 10 sec and held for 3 min and 1 hr. Bacterial reductions were calculated due to treatment by comparing bacterial populations recovered before and after treatment. Bacteria were enumerated on tryptic soy agar (TSA).

TABLE 5

| Cutting Board Area 769 cm$^2$ | Bacterial Count Recovered | Bacterial Reduction |
|---|---|---|
| Control (No Treatment) | 4.12 Log CFU/cm$^2$ | |
| Treatment (10 s spray with 8 ml nozzle, 1 hr hold time) | 3.26 Log CFU/cm$^2$ | 0.86 Log CFU/cm2 |

TABLE 6

| Cutting Board Area 644.35 cm$^2$ | Bacterial Count Recovered | Bacterial Reduction |
|---|---|---|
| Control (No Treatment) | 4.46 Log CFU/cm$^2$ | |
| Treatment (10 s spray with 8 ml nozzle, 3 min hold time) | 3.41 Log CFU/cm$^2$ | 1.05 Log CFU/cm2 |

Various modifications and variations of the described methods and compositions of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control.

What is claimed is:

1. An antimicrobial composition comprising an organic acid and an organic citrus extract, wherein the organic acid is a buffered vinegar at a concentration of approximately 90% to approximately 99.5% w/v, wherein the buffered vinegar is buffered to a pH of 6.1±0.1, and wherein the organic citrus extract is derived from an albedo layer of a citrus fruit, a flavedo layer of a citrus fruit, or a combination thereof and is at a concentration of 0.1% to 5% w/v.

2. The antimicrobial composition of claim 1, wherein the organic acid, prior to buffering, has a pH of approximately 5.5 to approximately 7.3.

3. The antimicrobial composition of claim 2, wherein the organic acid, prior to buffering, has a pH of approximately 5.9 to approximately 7.1.

4. The antimicrobial composition of claim 1, wherein the organic acid is at a concentration of between approximately 95% to approximately 99.5% w/v.

5. The antimicrobial composition of claim 1, wherein the buffered vinegar comprises acetic acid and/or a consumable salt equivalent thereof.

6. The antimicrobial composition of claim 1, wherein the buffered vinegar comprises 0.5% to 8% acetic acid.

7. The antimicrobial composition of claim 6, wherein the buffered vinegar comprises 1% to 4% acetic acid.

8. The antimicrobial composition of claim 1, wherein the buffered vinegar is a corn vinegar, a sugar cane vinegar, a glacial acetic vinegar, an apple cider vinegar, or a combination thereof.

9. The antimicrobial composition of claim 1, wherein the organic citrus extract is at a concentration of 0.1% to 1% w/v.

10. The antimicrobial composition of claim 1, further comprising a masker, an emulsifier, or a combination thereof.

11. The antimicrobial composition of claim 10, wherein the masker is at a concentration of 0.05% to 0.2% w/v.

12. A method for reducing microbiological contamination on a food contact surface comprising applying the antimicrobial composition of claim 1 to the food contact surface in an amount effective to reduce or eliminate a microbial population on the food contact surface.

13. The method of claim 12, wherein the organic acid, prior to buffering, has a pH of approximately 5.5 to approximately 6.2.

14. The method of claim 12, wherein the buffered vinegar comprises 0.5% to 8% acetic acid.

15. The method of claim 12, wherein the buffered vinegar is a corn vinegar, a sugar cane vinegar, a glacial acetic acid vinegar, an apple cider vinegar, or a combination thereof.

16. The method of claim 14, wherein the antimicrobial composition is applied as a fine spray or mist.

17. The method of claim 12, wherein the antimicrobial composition is allowed to remain in contact with the food contact surface for at least 30 seconds prior to food coming into contact with the food contact surface.

18. The method of claim 17, wherein the food contact surface is a wood surface, a plastic surface, a rubber surface, a glass surface, or a stainless steel surface.

19. The method of claim 12, wherein the microbial population comprises one or more bacterial species and/or one or more fungal species.

20. The method of claim 19, wherein the bacterial species is a psychrotroph, a coliform, a lactic acid bacterial species, or a spore-forming bacterial species.

21. The method of claim 20, wherein the bacterial species is a *Pseudomonas* species, a *Micrococcus* species, an *Aerococcus* species, a *Lactococcus* species, *Leuconostoc* species, a *Streptococcus* species, a *Bacillus* species, a *Clostridium* species, a *Eubacterium* species, an *Enterococcus* species, or a *Listeria* species.

22. The method of claim 21, wherein the bacterial species is a *Listeria* species.

23. The method of claim 22, wherein the bacterial species is *L. monocytogenes*.

24. The method of claim 19, wherein the one or more fungal species comprises one or more yeast.

25. The method of claim 24, wherein the yeast is a *Geotrichum* species, a *Saccharomyces* species, a *Hansenula* species, a *Candida* species, a *Kluyveromyces* species, a *Debaryomyces* species, a *Pichia* species.

* * * * *